(12) United States Patent
Nagata

(10) Patent No.: US 6,622,575 B1
(45) Date of Patent: Sep. 23, 2003

(54) FINGERTIP-MOUNTED SIX-AXIS FORCE SENSOR

(75) Inventor: Kazuyuki Nagata, c/o Electrotechnical Laboratory, Agency of Industrial Science & Technology 1-4 Umezono 1 Chome, Tsukuba-shi, Ibaraki (JP)

(73) Assignees: Agency of Industrial Science and Technology; Ministry of International Trade and Industry, Tokyo (JP); Kazuyuki Nagata, Tsukuba (JP)

( * ) Notice: Subject to any disclaimer, the term of this patent is extended or adjusted under 35 U.S.C. 154(b) by 39 days.

(21) Appl. No.: 09/610,968

(22) Filed: Jul. 6, 2000

(30) Foreign Application Priority Data

Jul. 7, 1999 (JP) ............................. 11-193719

(51) Int. Cl.[7] ................................ G01D 7/00
(52) U.S. Cl. ........................... 73/862.042; 73/862.381
(58) Field of Search ..................... 73/862.042, 862.041, 73/862.043, 862.044, 862.045, 862.046, 862.05, 862.629, 862.636, 862.631

(56) References Cited

U.S. PATENT DOCUMENTS

| | | | | |
|---|---|---|---|---|
| 3,948,093 A | * | 4/1976 | Folchi et al. | 73/862.044 |
| 4,094,192 A | * | 6/1978 | Watsen et al. | 73/862.044 |
| 4,982,611 A | | 1/1991 | Lorenz et al. | |
| 5,212,372 A | * | 5/1993 | Quick et al. | 235/462.044 |
| 5,316,017 A | * | 5/1994 | Edwards et al. | 600/595 |
| 5,365,799 A | | 11/1994 | Okada et al. | |
| 5,423,332 A | * | 6/1995 | Zirps et al. | 600/587 |
| 5,526,700 A | * | 6/1996 | Akeel | 73/862.043 |
| 5,631,861 A | * | 5/1997 | Kramer | 364/406 |
| 5,648,617 A | | 7/1997 | Cullen et al. | |
| 5,868,357 A | * | 2/1999 | Gabriel | 244/137.1 |
| 5,889,214 A | * | 3/1999 | Kang et al. | 73/862.044 |
| 5,911,693 A | * | 6/1999 | Prochazka et al. | 600/587 |
| 6,035,274 A | * | 3/2000 | Kramer et al. | 704/270 |
| 6,042,555 A | * | 3/2000 | Kramer et al. | 600/595 |
| 6,059,506 A | * | 5/2000 | Kramer | 414/5 |
| RE37,065 E | * | 2/2001 | Grahn | 73/628 |

FOREIGN PATENT DOCUMENTS

| | | |
|---|---|---|
| DE | 237213 A1 | 5/1985 |
| DE | 69222745 T2 | 2/1993 |
| JP | 4-40333 | 2/1992 |
| JP | 5-149811 | 6/1993 |
| JP | 5-506736 | 9/1993 |
| JP | 6-182688 | 7/1994 |
| JP | 10-249768 | 9/1998 |
| WO | WO 91/11775 | 8/1991 |

OTHER PUBLICATIONS

Yoji Yamada, "Sensing Strategies Before Grasping Part 2 Detection of Slip and Static Friction Coefficient Used to Acquire Information on Surface Roughness," Journal of the Robotics Society of Japan, vol. 11, No. 7, (Aug. 12, 1993), pp. 959–965.

(List continued on next page.)

Primary Examiner—Edward Lefkowitz
Assistant Examiner—Andre Allen
(74) Attorney, Agent, or Firm—Oblon, Spivak, McClelland, Maier & Neustadt, P.C.

(57) ABSTRACT

A fingertip-mounted six-axis force sensor includes a fingerstall into which a fingertip of a human is inserted, an elastic component connected and fixed to the fingerstall, adapted to distort in response to specific force components including fingertip contact forces and contact moments, and equipped with a distortion detecting device for detecting force components in three axial directions, and a finger cover equipped with a fitting block and connected and fixed to the elastic component via the fitting block. Distortion of the elastic component produced in response to the fingertip contact forces and contact moments exerted onto an object by the human fingertip is detected by the distortion detecting device and converted into an electrical signal that is taken out and processed to calculate the fingertip contact forces.

5 Claims, 2 Drawing Sheets

OTHER PUBLICATIONS

The Glove Scan System, NITTA Co.

Kazuyuki Nagata, et al., "Development of a Fingertip–type 6D Force Sensor and Error Evaluation of Contact Point Sensing," Journal of the Robotics Society of Japan, vol. 14, No. 8, (Nov. 1996), pp. 1221–1228. (with English Abstract).

Shunji Shimizu, et al., "Development of Sensor Glove MKIII For Measuring Grasping Pressure Distribution," The $14^{th}$ Science Lecture Meeting of the Robotics Society of Japan, (1996), 1075–1076. (with English Abstract).

* cited by examiner

FINGERTIP-MOUNTED SIX-AXIS FORCE SENSOR

BACKGROUND OF THE INVENTION

1. Field of the Invention

The present invention relates to a six-axis force sensor mounted on the fingertip of a human for analyzing a grasping operation made by the human and detecting a contact force during the grasping operation so that a robot can conduct the same grasping operation in accordance with the analyzed and detected data. This sensor is also applicable to a force display device that gives a human a sensation of actual existence of virtual data stored in a computer.

2. Description of the Prior Art

As conventional six-axis force sensors, there have been developed the one mounted on the wrist of a robot (e.g. six-axis force sensor IFS series by NITTA Co.) and the one mounted on the fingertip of a robot hand (e.g. NANO sensors by BL Autotech Ltd.). As conventional tactile sensors mounted on a hand of a human being to detect distribution of pressures applied onto the fingers and palm, a glove-shaped tactile sensor for pressure distribution using pressure-sensible conductive rubber and a conductive ink sheet (e.g. the glove scan system by NITTA Co.) has been developed, for example.

In order to skillfully manipulate a given object with the fingertips of a robot hand, it is at first necessary to analyze a grasping operation conducted with a hand of a human being. In order to analyze such human manipulation, it is necessary to detect the finger motion and contact force acting on the fingertip.

The glove scan system developed by NITTA Co. has been cited above as a sensor for detecting a pressure distribution onto a hand of a human being. Another example is a sensor glove having a distributed tactile sensor sewed onto a glove [Shimizu et al., "Development of Sensor Glove MK III for measuring grasping pressure distribution," The 14th Science Lecture Meeting of the Robotics Society of Japan, 1996].

These sensor gloves can detect distribution of pressures applied onto the fingers and palm. However, the detected force components are those of the force exerted only in the direction perpendicular to the surface of the sensor. In other words, forces exerted in the direction horizontal to the sensor surface, including a shearing force and a frictional force, and a contact moment on the sensor surface cannot be detected by the sensor gloves.

On the other hand, it has been known that the grasping force used when a human being grasps a given object is a critical point to induce a slip between the given object and the fingers [Yamada, "Detection of Slip and Static Friction Coefficient,"Journal of the Robotics Society of Japan, Vol. 11, No. 7, 1993]. This indicates that a human being pays his attention to not only the perpendicular force, but also the horizontal force relative to the finger surface when grasping a given object.

It has also pointed out that a human being utilizes a frictional force (the force in the direction horizontal to the finger surface) and a contact moment on the finger surfaces when manipulating a given object. In order to use data detected from demonstration manipulation by a human being directly for the control of a robot hand, it is desirable that data of a sensor identical with the sensor mounted on the robot hand be analyzed.

It is reported that it is important to use a six-axis force sensor as a sensor to be mounted on the fingertip of a robot hand [Nagata et al., "Development of a Fingertip-type 6D Force Sensor and Error Evaluation of Contact Point Sensing," Journal of the Robotisc Society of Japan, Vol. 11, No. 7, 1993]. From this point of view, it has been desired to use, as a sensor mounted on a hand of a human being for detecting the contact force, a six-axis force sensor that can detect forces and moments in the three axial directions There have heretofore been developed six-axis force sensors for robots. Of these sensors, NANO sensors produced by BL Autotech Ltd. have the smallest size that is 18 mm in diameter and 32.8 mm in length. This size is too large to mount such a NANO sensor on the fingertip of a human being.

The present invention has been accomplished in view of the above. An object of the present invention is to provide a six-axis force sensor capable of being mounted on the fingertip of a human being.

SUMMARY OF THE INVENTION

To attain the above object, the present invention provides a fingertip-mounted six-axis force sensor comprising a fingerstall into which a fingertip of a human being is inserted, an elastic component connected and fixed to the fingerstall, easy to distort in response to force components (that comprise fingertip contact forces and contact moments throughout the description) and equipped with distortion detecting means, and a finger cover equipped with a fitting block and connected and fixed to the elastic component via the fitting block, wherein distortion of the elastic component produced in response to the contact force and moment exerted onto an object by the human fingertip is detected by the distortion detecting means and converted into an electrical signal that is taken out and calculation-processed to detect the fingertip contact forces.

The elastic component may comprise a base connected to the fingerstall, a peripheral ring fixed to the fitting block, four beams that connect the base and the peripheral ring, and distortion detecting means, such as strain gauges or optical sensor units, attached to the surfaces of each beam. When a force is exerted onto the elastic component in the direction of the x-axis or y-axis, the two beams disposed perpendicular to the force-exerted direction distort. When a force is exerted onto the elastic component in the direction of the z-axis, all the beams distort. When a moment acts on the elastic component about the z-axis, all the beams distort. When a moment acts on the elastic component about the x-axis or y-axis, the two beams disposed perpendicular to the moment-acting axis distort. The distortion of the beams is detected by the distortion detecting means such as strain gauges. Thus, the contact force and moment when grasping an object with the fingertips of a human being can be detected.

The above and other objects and features of the present invention will become apparent from the accompanying drawings and following detailed description.

BRIEF DESCRIPTION OF THE DRAWINGS

FIG. 1(*b*) is a cross section taken along line I(*b*)—I(*b*) in FIG. 1.

DESCRIPTION OF THE PREFERRED EMBODIMENT

The present invention will be described in detail with reference to one embodiment of a fingertip-mounted six-axis force sensor shown in the accompanying drawings.

Figure 1A:
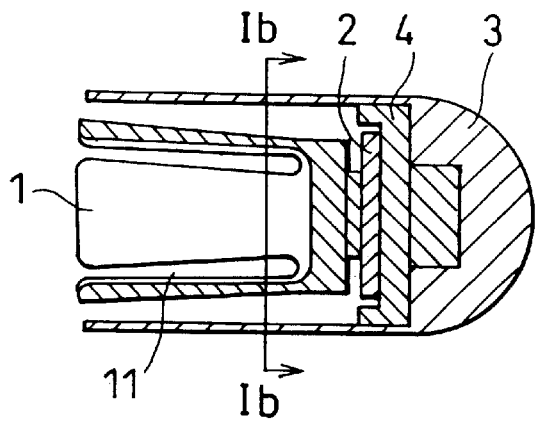
FIG. 1(*a*) is a cross section showing the fundamental construction of a finger-mounted six-axis sensor according to the present invention.
Figure 1B:
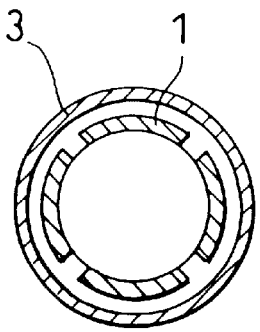

As shown in FIGS. 1(a) and 1(b), the sensor comprises a fingerstall 1, an elastic component 2 and a finger cover 3. The finger cover 3 is a part in contact with an object and has a fitting block 4 which is fixed to the inside of the finger cover 3 and through the fitting block 4 the finger cover 3 is connected and fixed to a peripheral ring 22 of the elastic component 2 which will be described later. The finger cover 3 has to be made of a material difficult to deform and induce a slip between an object and the fingers grasping the object, such as aluminum or hard plastic coated with silicone rubber.

Figure 2:
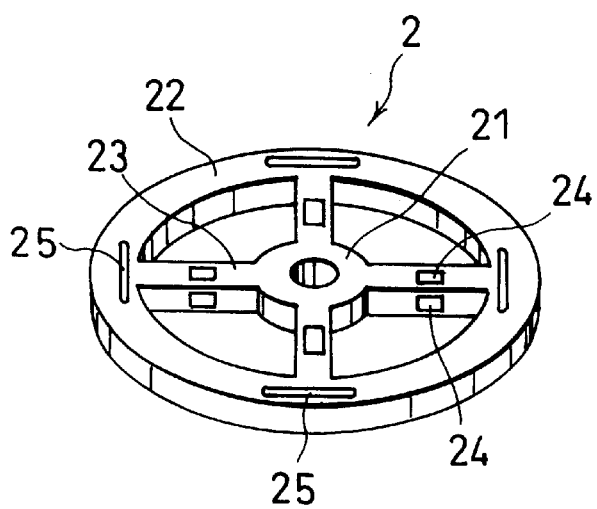
FIG. 2 is a perspective view showing one example of an elastic component used in the sensor of FIG. 1.

The elastic component 2 is easy to distort in response to specific force components (force and moment). FIG. 2 shows one example of the elastic component 2, that comprises a base 21, a peripheral ring 22, four beams 23 that connects the base 21 and the peripheral ring 22 (a cross beam structure). A strain gauge 24 is attached to each of the right and left vertical surfaces and top and bottom horizontal surfaces of each beam 23. Bellows 25 is disposed on the peripheral ring 22 at each position of connection with the beams 23. When an external force is exerted onto the elastic component 2, the beams 23 distort. This distortion is converted into an electrical signal by the strain gauges 24 to enable the force components to be taken out in the form of the electrical signal. Optical sensor units can be used in place of the strain gauges. The peripheral ring 22 of the elastic component 2 is fixed to the fitting block 4 of the finger cover 3 by means of screws or other such means. In addition, the base 21 and beams 23 are not in contact with the fitting block 4 in the presence of a recess formed in the fitting block 4 even when distorting by an external force.

A strain stiffness matrix expressing the relationship between the six-axis forces (forces and moments in the three directions) exerted onto the elastic component 2 and the outputs of the strain gauges of each beam, is obtained in advance by calibration and is a matrix for converting the outputs of the strain gauges of each beam into forces. The six-axis forces exerted onto the elastic component 2 can be calculated from the output signals of the strain gauges using the strain stiffness matrix.

The fingerstall 1 is a part for insertion of a fingertip of a human being and is made of a resilient material, such as engineering plastic, phosphor bronze, spring steel, etc., formed with cuts 11 in consideration of the difference among individual fingertip sizes, and connected to the base 21 of the elastic component 2. Further, the finger convert 3 may be connected to the base 21 of the elastic component 2 while the fingerstall 1 may be connected to the peripheral ring 22.

Figure 3:
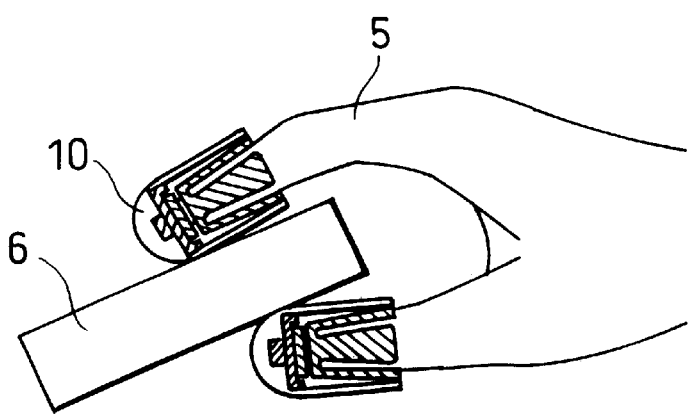
FIG. 3 is an explanatory view showing the operation of the sensor according to the present invention.

The operation of the embodiment will be described. As shown in FIG. 3, a human being inserts his finger 5 into the fingerstall 1 of the fingertip-mounted six-axis force sensor according to the present invention and grasps an object 6. The structure of the sensor is made transparent in the drawings for easy reference. He exerts force to the grasped object 6 via the fingerstall 1, elastic component 2 and finger cover 3, with the finger cover 3 in contact with the given object 6.

The beams 23 of the elastic component 2 disposed between the fingerstall 1 and the finger cover 3 distort in response to the contact forces and moments exerted onto the object 6 by the finger 5. This distortion is converted into an electrical signal by the strain gauges 24 and read in a computer (not shown) via an A/D convertor (not shown). His force exerted onto the given object 6 can be calculated from the output signals of the strain gauges using the strain stiffniess matrix obtained in advance by calibration.

Figure 4A:
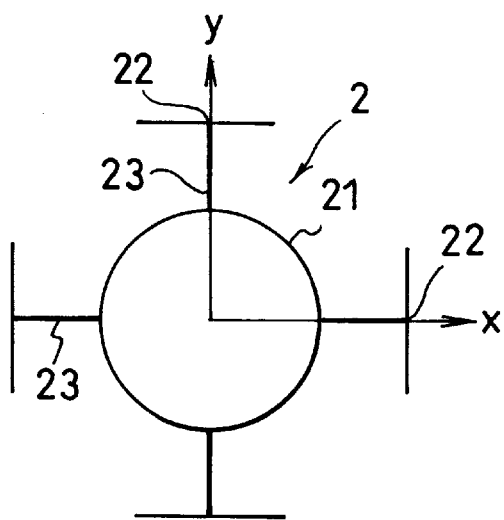
FIG. 4(a) is a plan view showing the elastic component when no force is exerted thereto.
Figure 4B:
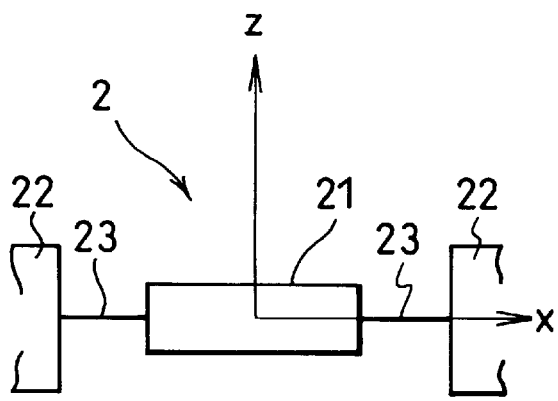
FIG. 4(b) is a side view showing the elastic component of FIG. 4(a).

The concrete principle of detection of six-axis forces exerted onto the elastic component will be described with reference to FIG. 4. FIG. 4(a) is a plan view of the elastic component having a cross beam structure and FIG. 4(b) is a side view thereof The distortion detecting means is omitted from FIG. 4.

Figure 4C:
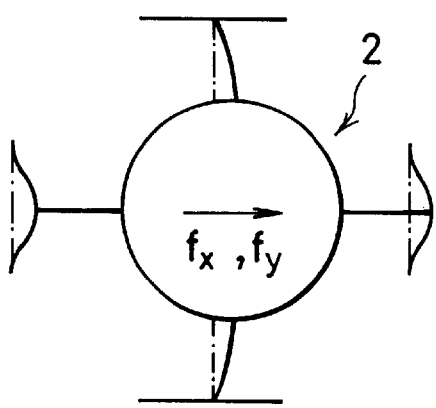
FIG. 4(c) is a plan view showing the elastic component when a force is exerted thereto in the direction of the x-axis or y-axis.

When a force $f_x$ or $f_y$ is exerted onto the elastic component 2 in the direction of the x-axis or y-axis, the two beams of the elastic component disposed in the direction perpendicular to the force-exerting direction distort, as shown in FIG. 4(c), in accordance with the intensity of the exerted force. This distortion is measured by the strain gauges on the opposite right and left sides of each beam. On the other hand, the two remaining beams disposed in the force-exerted direction do not distort while the bellows on the peripheral ring facing the two remaining beams distort.

Figure 4D:
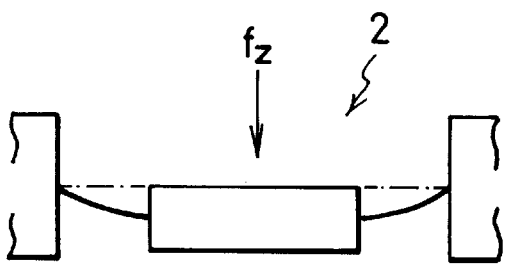
FIG. 4(d) is a side view showing the elastic component when a force is exerted thereto in the direction of the z-axis.

When a force $f_z$ is exerted onto the elastic component in the direction of the z-axis, all the beams of the elastic component 2 distort in accordance with the intensity of the exerted force as shown in FIG. 4(d). This distortion is measured by the strain gauges on the top and bottom sides of each beam.

Figure 4E:
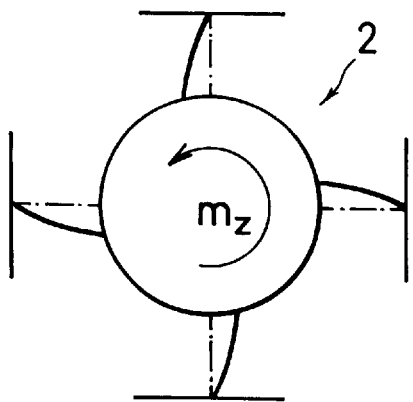
FIG. 4(e) is a plan view showing the elastic component when a moment acts thereon about the z-axis.

When a contact moment $m_z$ acts on the elastic component about the z-axis, all the beams distort as shown in FIG. 4(e). This distortion is measured by the strain gauges on the opposite right and left sides of each beam.

Figure 4F:
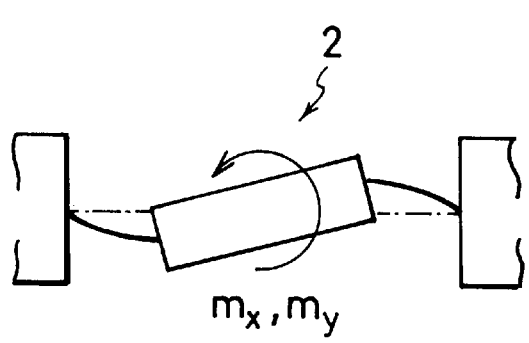
FIG. 4(f) is a side view showing the elastic component when a moment acts thereon about the x-axis or y-axis.

When a contact moment $m_x$ or $m_y$ acts on the elastic component about the x-axis or y-axis, the two beams disposed in the direction perpendicular to the moment-acting axis distort, as shown in FIG. 4(f), in accordance with the intensity of the acting moment. This distortion is measured by the strain gauges on the top and bottom sides of each beam.

Thus, the six-axis forces exerted onto the elastic component can be calculated from the output signals of the strain gauges.

While the present invention has been described in the foregoing with reference to one embodiment of the fingertip-mounted six-axis force sensor, it is not limited to the embodiment but can be modified within the scope of the appended claims.

While the elastic component has a cross beam structure, it may have a three-beam structure or may be of a parallel plane type or a ring type insofar as it can detect six-axis forces and can be made compact.

Since the present invention is constituted as described above, it is possible to detect forces and moments in the three axial directions. That is to say, the present invention can detect not only the forces vertical to the sensor surface, but also the shearing force and frictional force that are the forces horizontal to the sensor surface and the contact moments on the sensor surface. Therefore, it is possible to detect the contact force and moment when grasping an object with the human fingertips.

If the fingertip of a human being is equipped with a sensor for detecting data identical with the data of a sensor mounted on the fingertip of a robot hand and data detected from his demonstrating manipulation are analyzed, the analyzed date can be used directly for the control of a robot hand to enable the robot hand to make a dexterous manipulation same as his demonstrating manipulation.

What is claimed is:

1. A fingertip-mounted six-axis force sensor comprising:
   a fingerstall into which a fingertip of a human is inserted;
   a distortion detecting device configured to detect force components;
   an elastic component connected and fixed to the fingerstall, adapted to distort in response to specific force components including fingertip contact forces and contact moments, and equipped with the distortion detecting device; and
   a finger cover equipped with a fitting block and connected and fixed to the elastic component by the fitting block;
   wherein distortion of the elastic component produced in response to the fingertip contact forces and contact moments exerted onto an object by the human fingertip is detected by the distortion detecting device and converted into an electrical signal that is taken out and processed to calculate the fingertip contact forces.

2. A fingertip-mounted six-axis force sensor according to claim 1, wherein said elastic component comprises a base connected to the fingerstall, a peripheral ring connected and fixed to the fitting block, four beams each having one end connected to the base and an opposite end connected to the peripheral ring, and the distortion detecting device mounted on each beam.

3. A fingertip-mounted six-axis force sensor according to claim 1, wherein said elastic component comprises a base connected to the fingerstall, a peripheral ring connected and fixed to the fitting block, three beams each having one end connected to the base and an opposite end connected to the peripheral ring, and the distortion detecting device mounted on each beam.

4. A fingertip-mounted six-axis force sensor according to claim 2, wherein said distortion detecting device comprises strain gauges.

5. A fingertip-mounted six-axis force sensor according to claim 3, wherein said distortion detecting device comprises strain gauges.

* * * * *